(12) United States Patent
Birchmeier et al.

(10) Patent No.: US 7,067,474 B1
(45) Date of Patent: Jun. 27, 2006

(54) AGENTS FOR TREATING HUMAN ILLNESSES BASED ON β-CATENIN, AND THE PRODUCTION AND USE THEREOF

(75) Inventors: Walter Birchmeier, Schwanebeck (DE); Jens-Peter Von Kries, Zepernick (DE)

(73) Assignee: Max-Delbruck-Centrum fur Molekulare Medizin (DE)

( * ) Notice: Subject to any disclaimer, the term of this patent is extended or adjusted under 35 U.S.C. 154(b) by 47 days.

(21) Appl. No.: 09/641,104

(22) Filed: Aug. 17, 2000

Related U.S. Application Data

(63) Continuation of application No. PCT/DE99/00554, filed on Feb. 21, 1999.

(30) Foreign Application Priority Data

Feb. 21, 1998 (DE) ................. 198 07 390

(51) Int. Cl.
*A61K 38/00* (2006.01)
*C07K 14/00* (2006.01)

(52) U.S. Cl. ..................... 514/2; 514/12; 530/300; 530/324; 530/350; 435/6; 435/7.1; 435/366

(58) Field of Classification Search ................. 514/12, 514/2; 530/300, 324, 350; 435/7.1, 6, 366
See application file for complete search history.

(56) References Cited

FOREIGN PATENT DOCUMENTS

| EP | 0757994 B1 | 2/1997 |
|---|---|---|
| WO | WO 96/16170 | 5/1996 |
| WO | WO 96/16170 A | 5/1996 |
| WO | WO 98/41631 | 9/1998 |
| WO | WO 98/42296 | * 10/1998 |
| WO | WO 98/45319 | 10/1998 |
| WO | WO 9842296 | 10/1998 |

OTHER PUBLICATIONS

Huber et al., Three-Dimensional Structure of the Armadillo Repeat of beta-Catenin, Cell 90, 871-882 (1997).*
Hülsken et al., E-Cadherin and APC Compete for the Interaction with beta-catenin and the Cytoskeleton, The Journal of Cell Biology 127, 2061-2069 (1994)..*
Tetsu O and McCormick F, "Beta-Catenin regulates expression of cyclin D1 in colon carcinoma cells" *Nature* (1999), vol. 398, pp. 422-426.

* cited by examiner

*Primary Examiner*—Jon Weber
*Assistant Examiner*—Chih-Min Kam
(74) *Attorney, Agent, or Firm*—Saliwanchik, Lloyd & Saliwanchik

(57) ABSTRACT

The present invention relates to peptides that affect the interaction of the protein β-catenin with a transcription factor or a tumor suppressor protein. Such peptides are derived either from the amino acids of β-catenin that are known to interact with such proteins, or from the amino acids of the transcription factor or tumor suppressor protein that are known to interact with β-catenin. The effect of the interaction is preferably inhibition of binding of β-catenin and the transcription factor or tumor suppressor protein. Peptide mutants and peptidomimetic compounds are also contemplated in the invention. The peptides, mutants and peptidomimetic compounds of the invention are useful for treating cancer in mammals, and particularly in humans.

5 Claims, 9 Drawing Sheets

Figure 1:
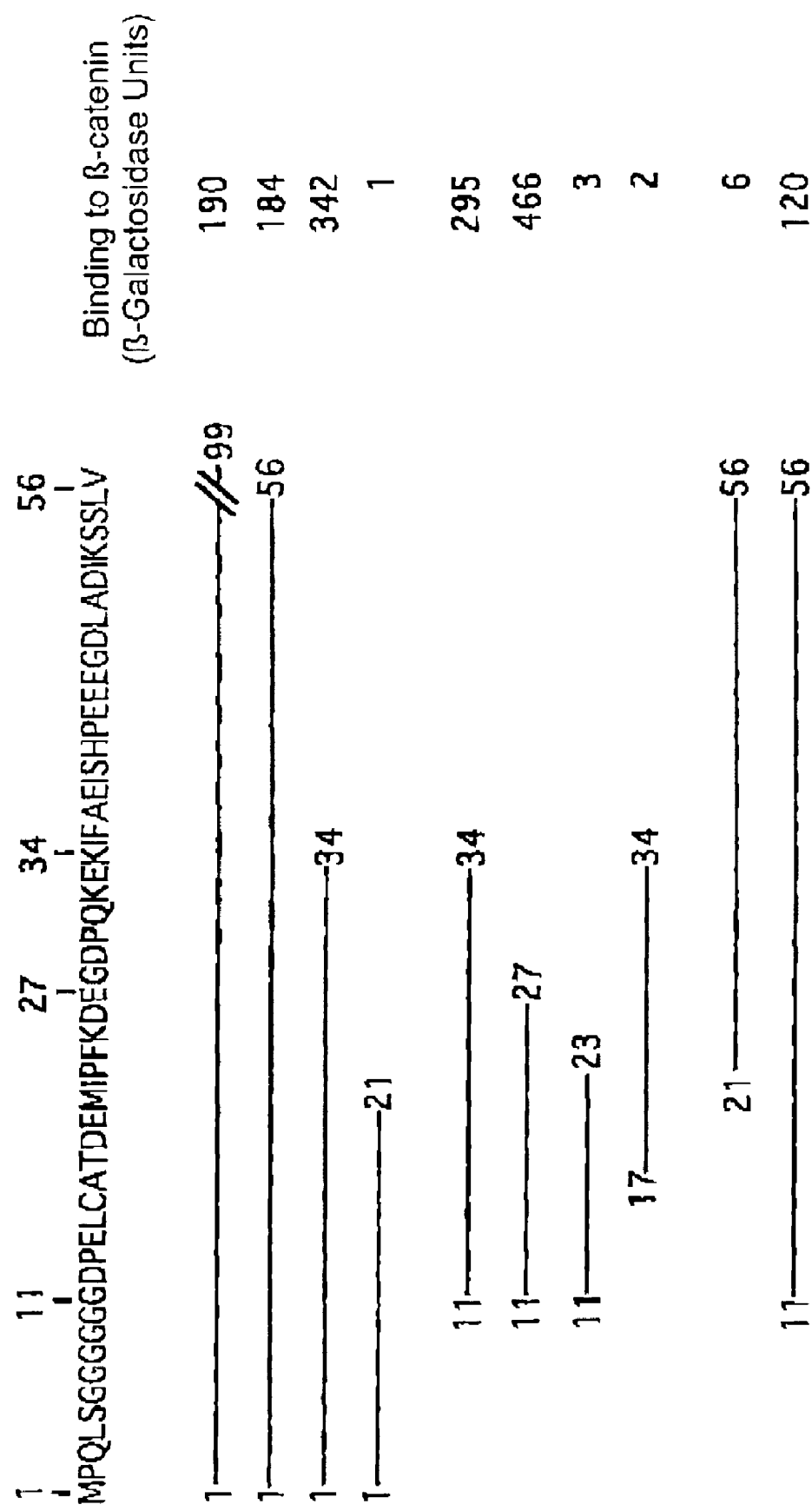

AGENTS FOR TREATING HUMAN ILLNESSES BASED ON β-CATENIN, AND THE PRODUCTION AND USE THEREOF

This application is a continuation of International Application No. PCT/DE99/00554, filed Feb. 21, 1999, which claims priority of German Patent Application No. 198 07 390.9, filed Feb. 21, 1998, the contents of which are incorporated herein by reference thereto.

DESCRIPTION

The invention relates to agents for treating human illnesses based on substances affecting the interaction between β-catenin and transcription factors and tumor suppressor gene products. Among them there are LEF-1-TCF-4-transcription factors and peptides derived from β-catenin and similar molecules. Furthermore, it relates to a method for detecting such substances and the use of the agent, preferably for treating tumors such as colonic cancers and melanomas.

Accordingly, fields of application of the invention are pharmaceutical industry and medicine.

β-catenin is a cytoplasmic protein which fulfils various functions in the cell. In complex with the cell adhesion molecules of the cadherin family β-catenin establishes the connection with the cytoskeleton (Huelsken J. et al., E-cadherin and APC compete for the interaction with beta-catenin and the cytoskeleton. J-Cell-Biol. 127: 2061–9, 1994). In addition, α-catenin is a component of the Wnt signal transduction which plays a big part in embryoic development. The transcription factor LEF-1 was identified as interaction partner of α-catenin in this signal cascade (Behrens, J. et al., Functional interaction of beta catenin with the transcription factor LEF-1. Nature, 382: 638–42, 1996). The mechanism of signal transduction by α-catenin and LEF-1 has been clarified: It consists of the transport of α-catenin into the cell nucleus mediated by LEF-1. This complex regulates the gene expression in the cell nucleus by the LEF-1 induced DNA flexion modified in the complex and by the carboxy-terminal transactivation domain of α-catenin. In the mean time, there has been shown that also other members of the LEF-1/TCF family of transcription factors, e.g. TCF-4, are able to mediate this signal transduction (Korinek, V. et al., Constitutive transcriptional activation by a beta-catenin-Tcf complex in APC-/-colon carcinoma. Science, 275: 1784–87, 1997).

Stabilizing the cytoplasmic pool of free β-catenin not bound to cadherin is the prerequisite to this signal transduction depending on β-catenin. This pool is negatively regulated by glycogen synthetase kinase 3β, by the tumor suppressor gene product APC and conductin/axin.

There was shown for cancers and melanomas that mutation. % in the N-terminal area of α-catenin or in the α-catenin binding domain of APC stop this regulation (Morin. P. J. et al., Activation of beta-catenin-Tcf signaling in colonic cancer by mutations in beta-catenin or APC. Science, 275: 1787–90, 1997). Accordingly, the β-catenin pool is stabilized. In melanomas this stabilization results in a LEF-1 mediated translocation of β-catenin into the cell nucleus whereas in colonic cancers this function is primarily fulfilled by TCF-4. The transcriptional activity of the complex in cancer cell lines is detected by activating a reporter gene. In addition, it has been shown that this activity is inhibited in APC-deficient colonic cancer cell lines after transfection of APC.

APC mutations were identified in the overwhelming majority of colonic cancers whereas not-APC-deficient tumors show mutations in the β-catenin gene. The result of these mutations of APC or β-catenin is an activation of signal transduction by the β-catenin-LEF/TCF complex. This underlines the key role played by β-catenin in the development of tumors. As APC mutations were identified as an early event in the development of colonic tumors the activation of the β-catenin-LEF/TCF complex is certainly a central step in the development of tumors.

Attempts have been made to utilize the key role played by β-catenin in the development of tumors for the development of therapeutic agents for treating tumors. Nearly at the same time, two patent applications were filed in the USA which, in the mean time, were published as WO papers. In WO 98/41631 (John Hopkins University—B. Vogelstein) the influence on interactions of β-catenin, TCF-4 and the tumor suppressor protein APC aimed at preventing the development of cancer is claimed. There was shown that products of mutated APC genes detected in colorectal tumors are no longer able to regulate the activation of the β-catenin/TCF-4 transcription. Furthermore, colorectal tumors with intact APC genes show activation mutations of β-catenin in the N-terminal area which affects the functioning of the most important phosphorylation sites. Based on this data, the conclusion is drawn that the regulation of β-catenin is critical for the tumor suppressor effect of APC and this regulation may be evaded by mutations in APC or in β-catenin. The main claim relates to the intron-free DNA molecule coding for TCF-4.

WO 98/42296 (Onyx Pharmaceuticals Inc.—Rubinfeld) relates to compositions and methods of diagnosing and treating illnesses caused by interactions between β-catenin and transcription factors. The main claim relates to the isolated, stabilized β-catenin and its fragments, yet such fragments were not indicated.

On the one hand the invention described here is aimed at making available new agents for treating cancers or aberrant tissue and organ developments. It is based on the special task to affect the interaction between β-catenin and LEF/TCF transcription factors as a prerequisite to the translocation and activity of the complex in the cell nucleus. This modulation shall be specific, i.e. it shall not interfere with other interactions of β-catenin (e.g. with APC, conductin or E-cadherin). In addition, the invention is aimed at developing ELISA methods for screening substance libraries to detect molecules (a. o. peptides, organic compounds) which highly specifically affect always only one interaction of β-catenin.

The invention is implemented according to the claims, the sub-claims are preferential variants.

Figure 2:
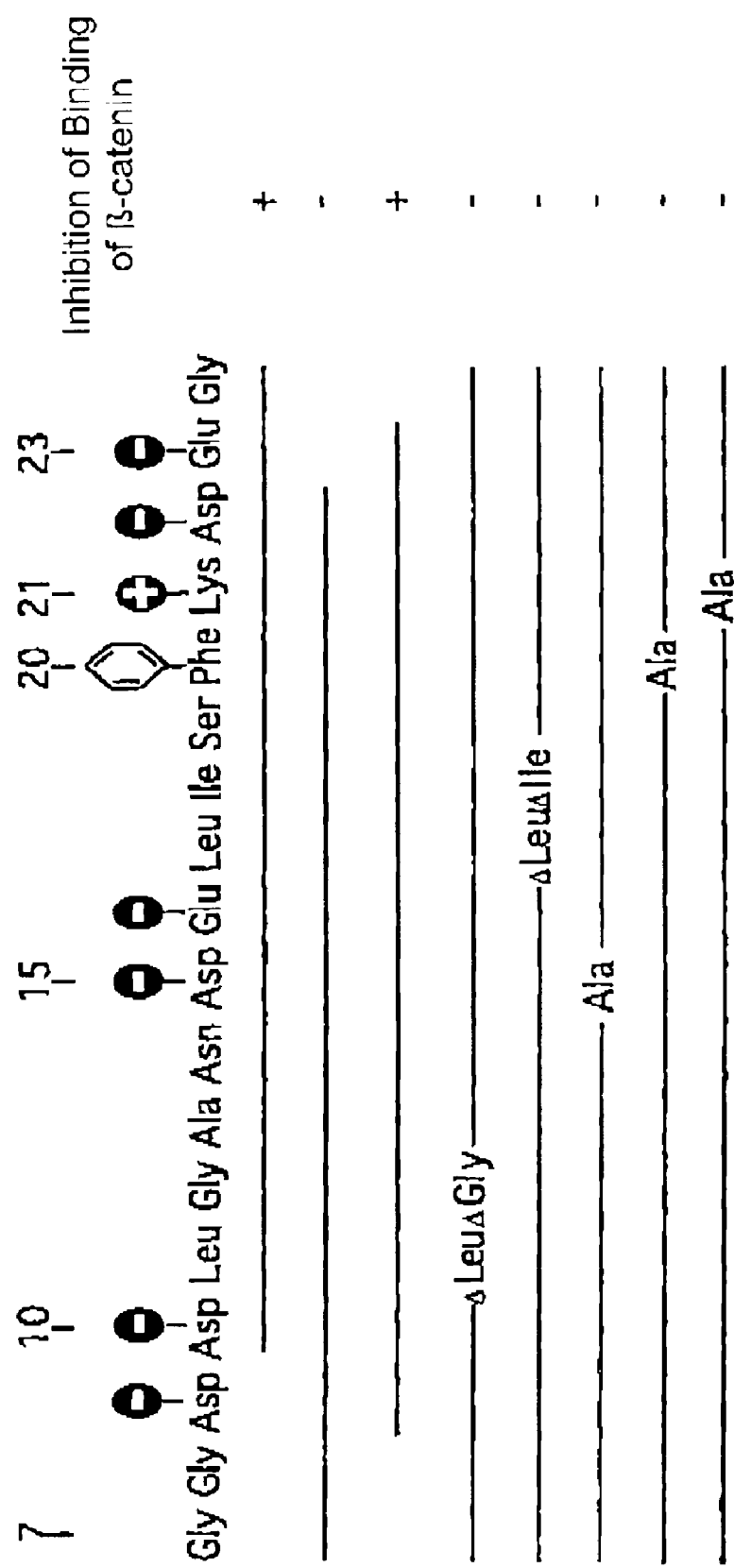

In a first implementation of the invention the binding domains of the LEF/TCF transcription factors for β-catenin were identified (FIG. 1). They are the starting point for obtaining peptides and similar molecules according to the invention. These peptides consist preferably of sequences containing 10–20 amino acids from the N-terminal domain of LEF-1 or TCF-4 (FIG. 2). These are especially preferably peptides consisting of the N-terminal amino acids 11–34 of LEF-1 (FIG. 1) with the following sequence Gly Asp Pro Glu Leu Cys Ala Thr Asp Glu Met Ile Pro Phe Lys Asp Glu Gly Asp Pro Gln Lys Glu Lys (SEQ. ID. NO.: 1)

consisting of the N-terminal amino acids 14–27 of LEF-1 with the following sequence Glu Leu Cys Ala Thr Asp Glu Met Ile Pro Phe Lys Asp Glu (SEQ. ID. NO.: 2)

consisting of the the N-terminal amino acids 7–29 (FIG. 2) with the following sequence Gly Gly Asp Asp Leu Gly Ala Asn Asp Glu Leu Ile Ser Phe Lys Asp Glu Gly Glu Gln Glu Glu Lys (SEQ ID. NO.: 3)

consisting of the N-terminal amino acids 10–23 of TCF-4 with the following sequence Asp Leu Gly Ala Asn Asp Glu Leu Ile Ser Phe Lys Asp Glu (SEQ. ID. NO. 4).

Furthermore, peptides where acid amino acids are arranged at a distance of 5 amino acids and flanked by hydrophobic and basic amino acids are preferred (FIG. 2).

These peptides may be used for treating tumors according to the invention with two principle ways being possible.

a) Use of peptides as such

A direct use of peptides for treating tumors is, in general, out of question owing to their instability towards proteases and owing to the lack of membrane permeability. Stabilizing is effected by coupling with a second peptide, for which the so-called antennapedia peptide Arg Gln Ile Glu Ile Trp Phe Gln Asn Arg Arg Met Glu Trp Glu Glu (SEQ. ID. NO.: 5) is excellently suited. This peptide is in a position to transport up to 100 amino acid long, coupled peptides through cell membranes into the cytoplasma and the cell nucleus. The coupled peptides may be used in treating tumors in a favourable way.

b) Use of peptides for drug design (peptide mimikry)

The peptides according to the invention serve also as a basis for designing substances which increase the stability and efficiency in the cell by a purposeful modification (peptidomimetics). This may be e.g. reached by adding reactive groups, substituting amino acids or design of non-hydrolizable peptide-like bonds.

By substituting the carbon skeleton of the peptides by synthetic carbon skeletons with the same arrangement of functional groups the stability of the molecules may be also increased (non-peptidomimetics). This molecular mimikry of the biological activity of inhibitory peptides derived from the minimum binding domain of LEF-1/TCF for β-catenin (FIGS. 3 and 4) allows the production of more potent agents for treating tumors.

Figure 5:
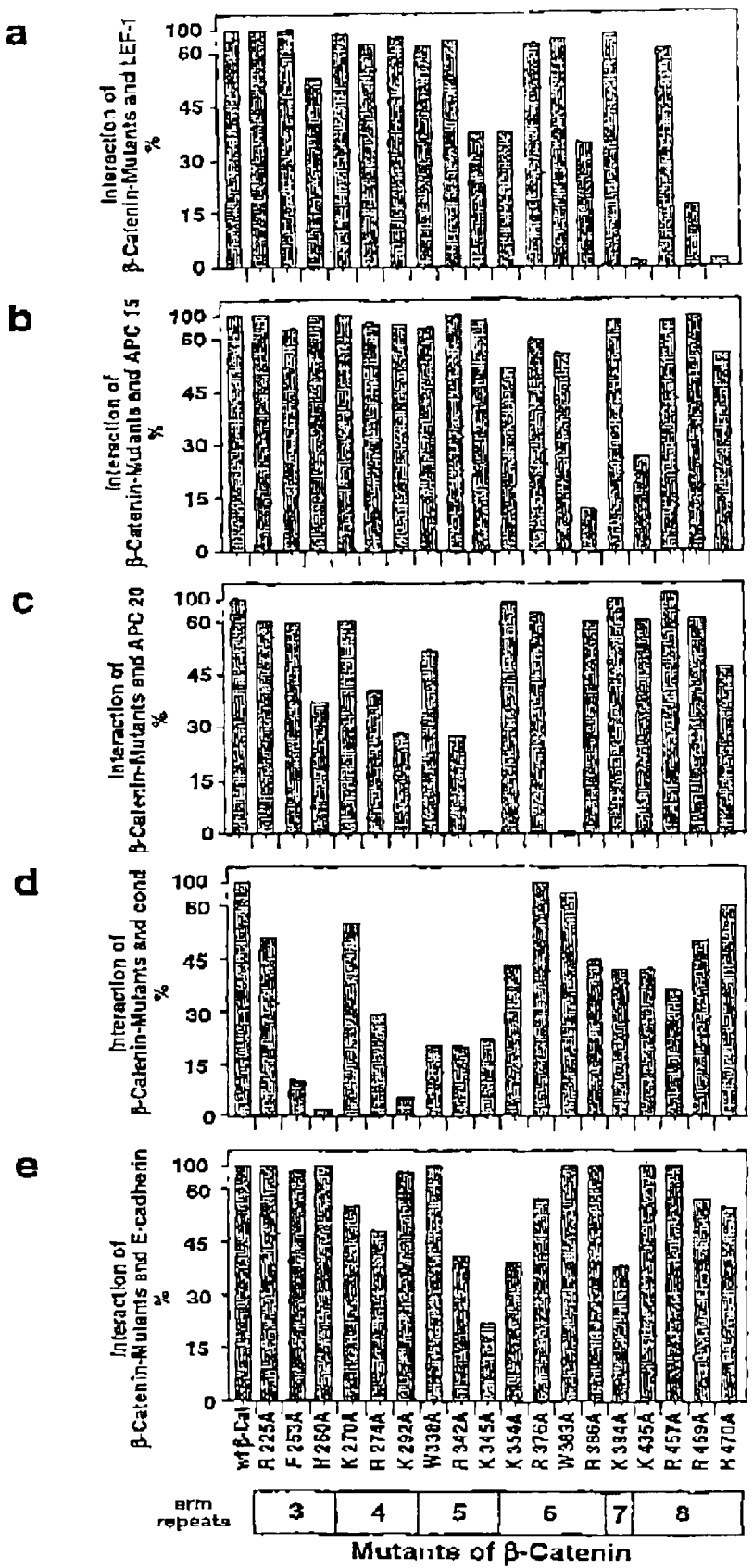
Figure 6:
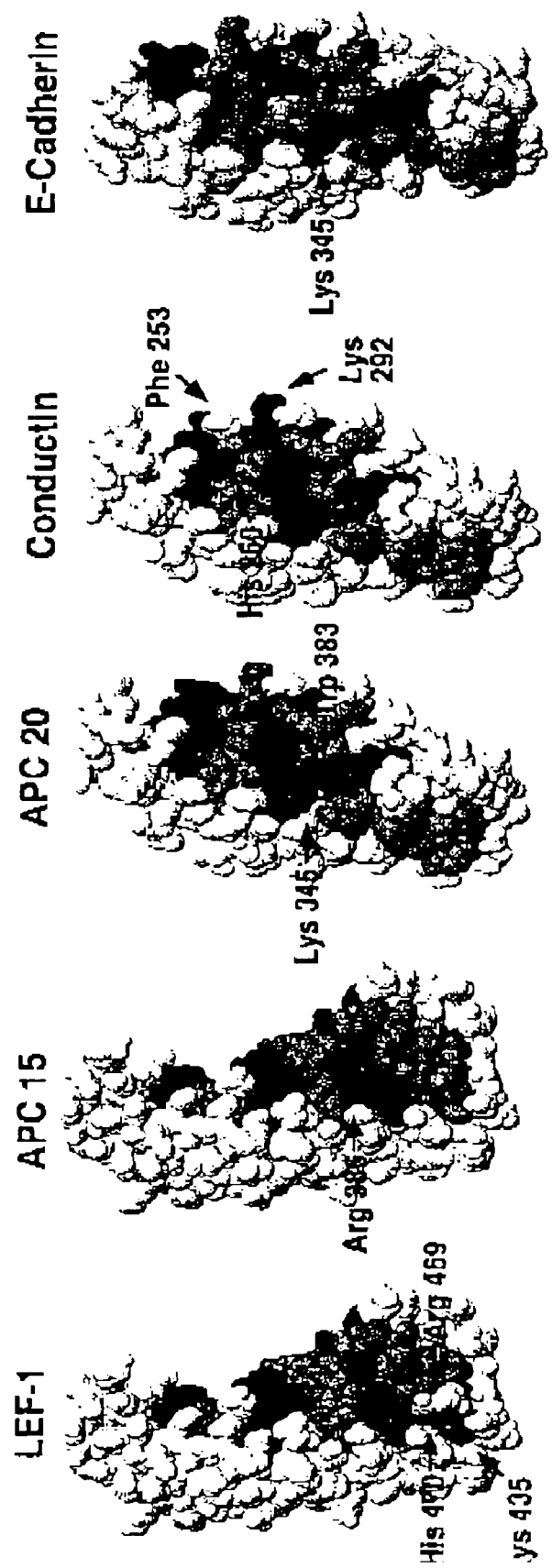
Figure 7:
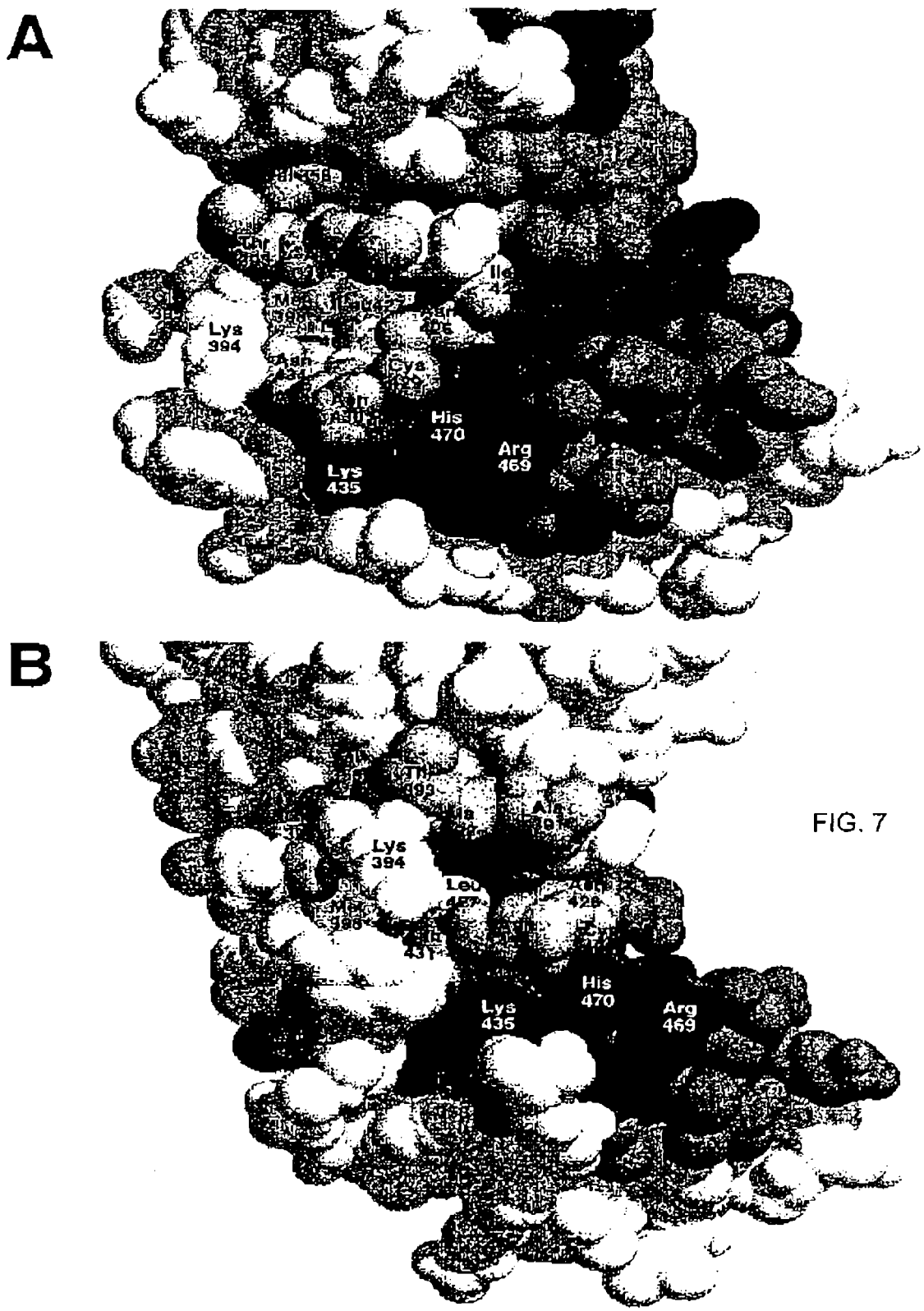

In a second step to implement the invention the regions of β-catenin which are responsible for the specific bonds with LEF-1/TCF-4. APC domains (containing 20 and 15 amino acid repeats), conductin and E-cadherin were identified. It was detected that these regions overlap partly and concern the armadillo domains 3–8 of β-catenin (FIGS. 5 and 6). The central point of this surprising finding is that mutations of β-catenin produced which prevent specific interactions with individual partners. In particular, the following mutations are concerned, related to the partial sequence of β-catenin described in the Annex (Tab. 1):

| | |
|---|---|
| His 470. Arg 469 | no interaction with LEF-1/TCF-4 |
| Trp 383 | no interaction with APC 20aa |
| Arg 386 | no interaction with APC 15aa |
| Phe 253, Arg 274, Trp | no interaction with conductin |

Thus, the possibility is provided the generate peptides and analogous molecules which specifically inhibit the interactions between β-catenin and APC. β-catenin and conductin or β-catenin and E-cadherin. These molecules are also suited to generate new pharmaca. To this end, potential candidates are brought into contact with β-catenin and e.g. LEF-1 under conditions when these proteins bind (e.g. in an ELISA) to achieve a cancerostatic effect. Then there will be measured to which extent this bond will be inhibited by the substance added. The Wnt signal transduction and its components play also a part in the development and maintenance of tissues and organs, e.g. of specific regions of the brain, extremities, the kidney and the skin. The tissue-specific knock out of the β-catenin gene in a mouse shows that β-catenin is of importance for the development of the skin and, in particular, of the hair. That is why the invention refers also to methods promoting the development of skin and hair by an increased expression of β-catenin (or of more stable β-catenin). This may be e.g. reached by inhibiting the interaction with APC or conductin.

Thus, according to the invention, specific inhibitors of the β-catenin/APC or β-catenin/conductin interaction may be used to reach increased β-catenin concentrations in cells and tissues. Equally conductin which is a protein analogous to axin promotes the degradation of β-catenin. Inhibitors of the interaction between β-catenin and APC and β-catenin and conductin may be used to interfere with processes of organ development. Thus, the development of hair of man could be e.g. locally promoted.

In particular, the following investigations were carried out:

1. Characterizing of the minimum binding domain of LEF/TCF for β-catenin:

The 'yeast-2-hybrid system' was used for identifying the minimum binding domain (FIG. 1). It was possible to limit the minimum binding domain to the N-terminal amino acids 11–27 of LEF-1 which corresponds t) the amino acids 7–29 in TCF-4 (FIG. 2). The interaction of N-terminal LEF-1 fragments with β-catenin was detected by means of activating a lacZ reporter gene (s. example).

In an ELISA with synthetic peptides there was shown that the respective peptides (11–34, 14–27) inhibit specifically the formation of the β-catenin/LEF-1 complex. Analogous principles apply to the TCF4 peptides 7–29 and 10–23 as regards the formation of the β-catenin/TCF-4 complex (FIG. 2).

The amino acids essential to the inhibition were identified by the synthesis of mutant peptides (FIG. 2). A symmetric arrangement of acid amino acids (aspartic acid and glutamic acid) at a distance of 5 amino acids flanked by hydrophobic amino acids (leucine, isoleucine) and a basic amino acid (Lys) is essential to the functioning of peptides. The substitution of phenyl alanine or lysine by alanine stops also the inhibition by the peptide. The importance of acid and aromatic amino acid residues was confirmed by a nucleus translocation test (FIG. 4) of endogenic β-catenin and by a transactivation test in mammalian cells in the context of the whole LEF-1 molecule.

2. Characterization of the interaction domain of β-catenin for LEF-1. APC conductin and E-cadherin The armadillo area of β-catenin was crystallized by Huber et al. in 1997 and characterized by the X-ray crystallographic analysis. It was possible to identify a basic groove which might be responsible for the interaction with the acid amino acids of LEF-1 (see above). That is why basic (Lys, Arg His) and some aromatic (Trp) amino acids were mutated in the armadillo repeat units 3–9 of β-catenin (FIG. 5). Attention was paid to the fact that notably free amino acid residues of helices 3 forming the basis of the groove and some amino acid residues of the periphery (helix 1) were mutated. The mutant β-catenins were tested if they still interact with the interaction partners LEF/TCF. APC, conductin and E-cadherin (Tab. 2). With the aid of this method it was possible to identify critical amino acid residues of β-catenin which are of importance to specific interactions (FIGS. 5 and 6). Thus it was possible to identify specific regions of β-catenin for the individual interaction partners (FIG. 6). These regions are important for identifying molecules affecting specifically the interaction of β-catenin with LEF-1, APC, conductin or E-cadherin.

The finding that the binding domains of β-catenin overlap partially for LEF-1/TCF, APC, conductin and E-cadherin is essential to the selection of new therapeutic agents. The selection is e.g. carried out in the following way: Substance libraries are tested whether they affect specifically the interaction between β-catenin and LEF-TCF, β-catenin and APC (20 or 15 amino acid repeats). β-catenin and conductin or β-catenin and E-cadherin. Thereupon, peptides or similar surface structures of the armadillo repeats 3–8 of β-catenin can be generated which were identified by mutation of β-catenin and these can subsequently be tested for their effect on binding of various interaction partners.

The interaction with LEF-1/TCF-4 is of an oncogenic nature, i.e. promotes potentially the development of cancer, the interactions with APC, conduction and E-cadherin are potentially anti-oncogenic, i.e. they inhibit the development of cancer. Each new substance interfering in the Wnt signal path has to be therefore carefully tested for its specific effect. The characterization of the binding domain of β-catenin presented here is the basis for that. Substances reducing specifically the β-catenin/LEF-1/TCF-4 interaction are therefore potential anti-cancer therapeutic agents. Substances inhibiting the interaction with APC, conductin or E-cadherin promote potentially the Wnt signal path and may be used for an intensified development of tissue, e.g. for promoting the growth of hair.

Hereinafter, the invention shall be explained in greater detail by way of examples:

1. Identification of the minimum binding domain of LEF-1 for β-catenin:

The interaction between the partial domains of LEF-1 and β-catenin was analyzed in the yeast-2 hybrid system by determining the activity of β-galactosidase according to information of the producer (Clontech) (FIG. 1). For this purpose the DNA coding for the N-terminal partial domains of LEF-1 was inserted into the cloning site of the Lex-A DNA binding domain which contains vector BTM 116 and checked by sequencing. The DNA fragments of LEF-1 were prepared by a polymerase chain reaction (PCR) and incubation with restriction endonucleases. The DNA coding for β-catenin was cloned into the vector pGAD424 (Clontech) for the activation domain of GAL-4 (Behrens et al. 1996). The β-galactosidase activities of independent experiments were averaged (or comparing the interaction of the hybrids.

The specificity of the interaction of the LEF-1 hybrids with β-catenin was checked by means of the β-galactosidase activity of yeasts producing the LEF hybrids and the GAL-4 activation domain without β-catenin (FIG. 1). The expression of the LEF-1 hybrids was checked in an immunoblot with yeast cell lysates by antibodies (Clontech) as against the Lex-A domain of the hybrids. Equal yeast quantities were used for preparing the lysates after determining the optical density of the cultures.

2. Characterization of the β-catenin binding domain of LEF-1 in the test for translation By an in vitro mutagenesis of the cDNA of LEF-1 point mutations were generated in the binding domain of LEF-1 for β-catenin. The mutagenesis was achieved by means of the "transformer site-directed mutagenesis kit" of the company Clontech according to information of the producer. The following amino acids were substituted by alanine: Glu 14, Asp 19, Glu 20, Phe 24, Lys 25, Asp 26 and Glu 27. The mutants were checked by sequencing and subcloned into the vector pCG-LEF-1 (Behrens et al. 1996). After the transfection of MDCK cells with LEF-1 or its mutants the translocation of endogenic & catenin into the cell nucleus was analyzed according to immunocytological methods. To this end, $2.5 \times 10^5$ MDCK cells were tranfected. The immunodetection of LEF-1 was carried out with an anti LEF-1 serum of rabbits and Cy2 conjugated anti-rabbit antibodies, the detection of β-catenin was achieved by means of monoclonal antibodies and Cy-3 conjugated anti-mouse antibodies (FIG. 4A).

Figure 3:
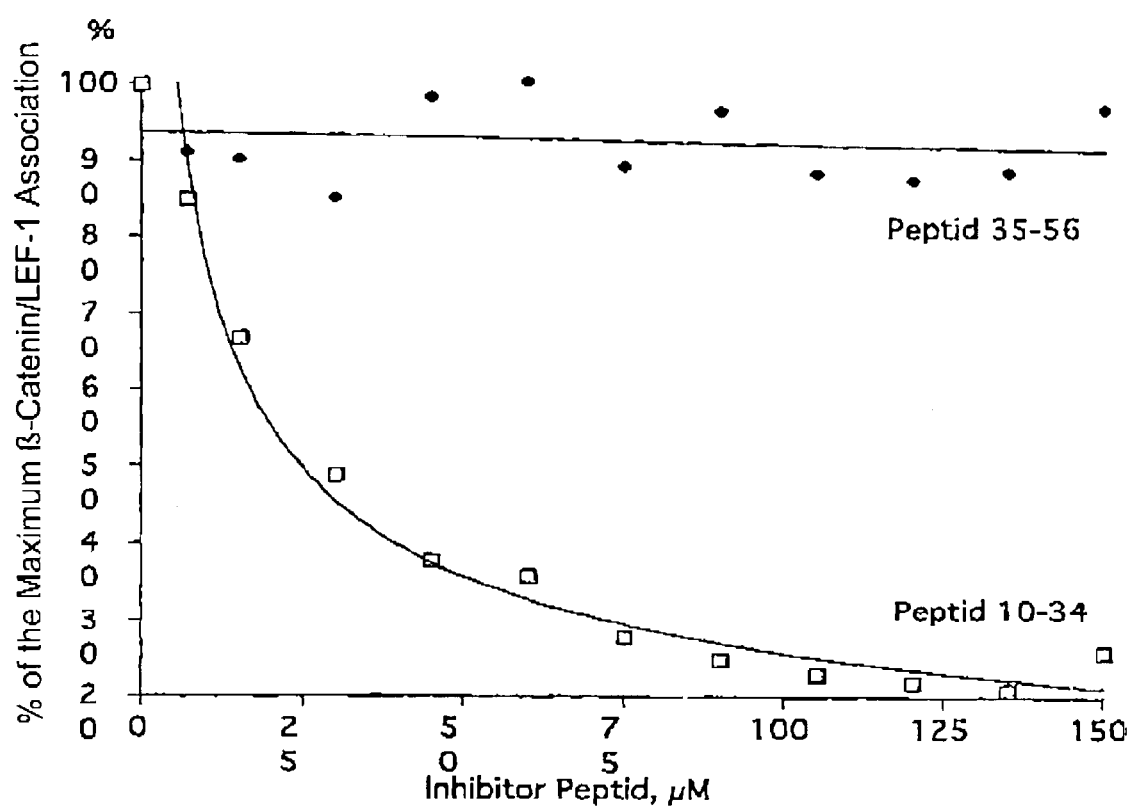
Figure 4:
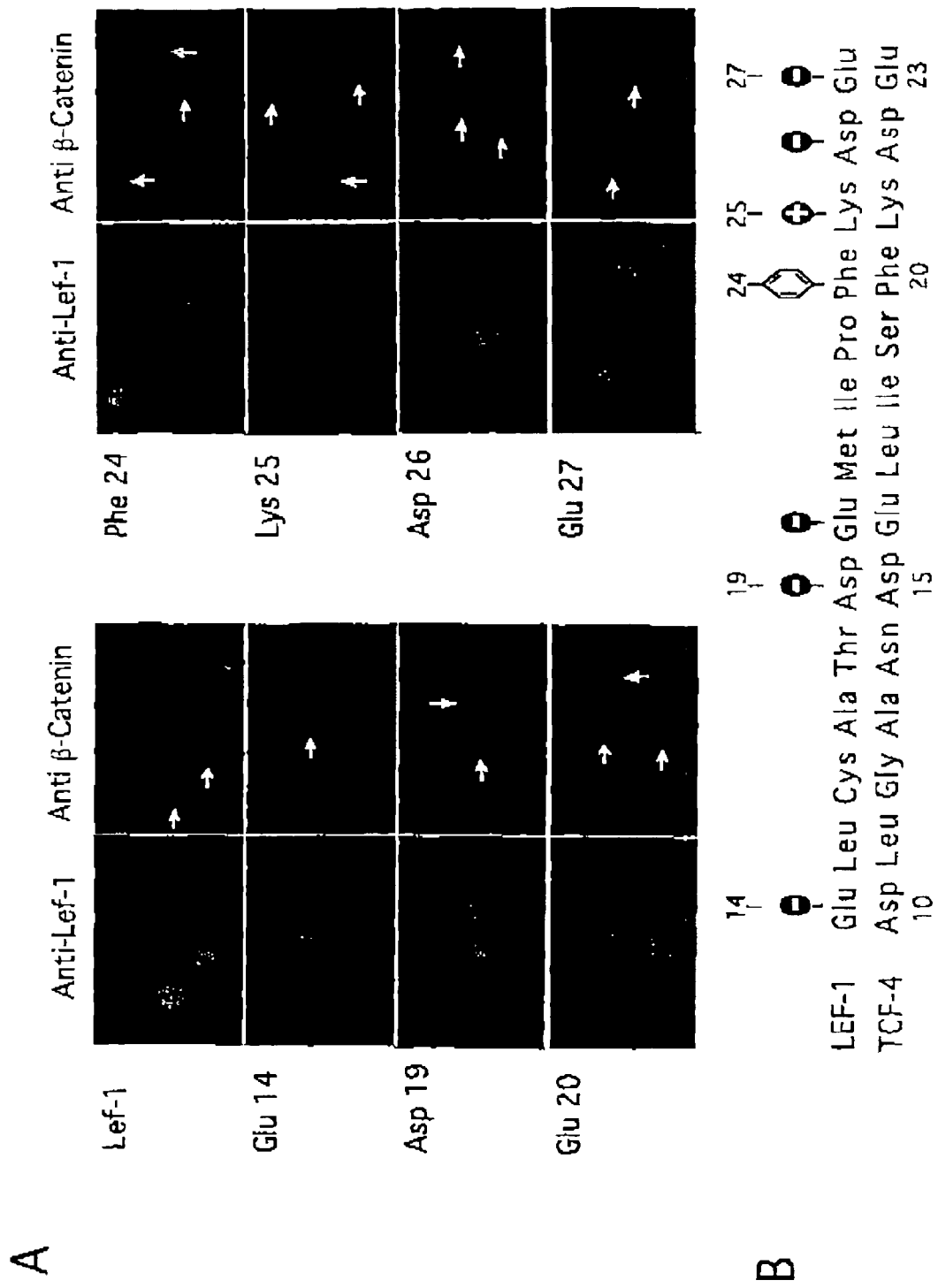

3. Characterization and quantification of inhibitory peptides in an ELISA:

Both proteins were produced in bacteria recombinantly with N-terminal histidine sequences, purified by means of nickel chromatography for quantifying the inhibition of the LEF-1/β-catenin interaction by synthetic peptides and (Behrens et al. 1996). The peptides were produced by the company Biosyntan with the aid of a PSSM-8 automaton (Shimadzu, Japan) applying the Fmoc/But strategy (E. Atherton and R. C. Sheppard. 1989 IRL Press. Oxford: "Solid phase peptide synthesis—a practical approach"). Approx. 50 ng of LFF-1 were absorbed in the wells of ELISA plates for 90 minutes at room temperature. Subsequently, the wells were covered with 5% dry milk powder in PBS for 16 hours at 4° C. All further steps were carried out at room temperature in PBS with 50 mM Tris HCl (pH 7.5). After washing the wells with PBS the peptide dilutions were added. The incubation with 50–100 ng of β-catenin was carried out for 10 minutes in the presence of 200 mg/ml BSA. The complex formation of LEF-1 and β-catenin was detected by the antibody PA2 against the carboxy terminal area of β-catenin (Huelsken et al. 1994). PA2 was added in a standard dilution of 1:5000 in 3% of dry milk powder in PBS for 10 minutes. After washing the wells with PBS a quantification was carried out by detection antibodies conjugated by peroxidase (1: 2500 in 3% of dry milk powder in PBS, Dianova) and the conversion of o-phenylenediamine was determined by photometric measurement at 405 mm. The peptides were used in concentrations of 100 µM to 0.3 µM. To check the specificity of the inhibition of the LEF-1/β-catenin interaction β-catenin was absorbed in the wells and detected by means of the same antibodies in the presence and absence of the peptides (FIGS. 2 and 3).

For a mutation analysis of the peptides the indicated amino acids were substituted by alanine during the synthesis. The inhibition of the complex formation of β-catenin and LEF-1 was quantified as has been already described (FIG. 2).

4. Preparation and testing of mutants of β-catenin modulating the interaction with LEF-1, APC, conductin or E-cadherin The mutagenesis of β-catenin in the armadillo repeats 3–8 was carried out by means of the "mutagenesis kit" of the company Clontech according to the producer's record and the mutants were checked by sequencing (FIG. 5). In all mutants the original amino acid was substituted by alanine. For analyzing the interactions the cDNA of human β-catenin (armadillo repeat 3 up to the C-terminal end of the protein) coding for the amino acids Leu218–Leu7 µl or its mutants was cloned into the fusion vector for the activation domain of Gal-4 (pGAD424, Clontech). The cDNA for the binding domains of the interaction partners was cloned into the Lex-A fusion vector BTM 116. To this end, the cDNA of LEF-1 for the amino acids 1–99, conductin for the amino acids Ala342–ARG465; of human APC for the amino acids His1012–Glu1215 (APC 15 amino acid repeats) and for the amino acids Ser1259Asp 1400 (APC 20 amino acid repeats) and E-cadherin for the amino acids Gin773–Asp884 (cytoplasmatic domain) were amplified with the respective primers PCR. The interaction of the Lex-A hybrids with β-catenin and its mutants was quantified by means of the β-galactosidase reporter activity in the yeast 2-hybrid system (report: "Matchmaker". Clontech) (Tab. 2 and FIG. 6).

LEGENDS FOR THE FIGURES AND TABLES

FIG. 1

Identification of the minimal binding domain of LEF-1 for β-catenin

The interaction of fragments of the binding domain of LEF-1 with β-catenin was analyzed by means of the β-galactosidase reporter activity in the yeast-2-hybrid system. The deletion of C-terminal amino acids of LEF-1 up to Glu27 and N-terminal amino acids up to Gly 10 does not result in a loss of bond (11–27) whereas further deletions prevent the interaction (11–23, 17–34). Accordingly, the minimum binding domain of LEF-1 for β-catenin consists of 17 amino acids (11–27) showing an acidic character. The partial domain of LEF-1 covering Met21 up to Val 56 does not show any binding activity towards β-catenin.

FIG. 2:

Characterization of the minimum binding domain of TCF-4 (residues 1–18 of SEQ ID NO: 3) by inhibition of binding of β-catenin to LEF-1 in an ELISA.

Synthetic peptides from the N-terminal area of hTCF-4 with substitutions of the amino acid residues indicated were tested for their ability to inhibit the interaction between LEF-1 and β-catenin. The substitution of the acid amino acid residues of Asp10, Asp15 and Asp22 of TCF-4 by alanine results in stopping the inhibition by the respective peptides. The substitution of Phe20 and Lys21 has the same effect. By a deletion an acid, minimum binding domain of TCF-4 for β-catenin of a length of 14 amino acids (Asp 10 up to Glu23) was identified.

FIG. 3:

Inhibition of the interaction between LEF-1 and β-catenin by synthetic peptides of the minimum binding domain of LEF-1 in an ELISA The synthetic peptide of the minimum binding domain of LEF-1 (10–34) inhibits the interaction between LEF-1 and β-catenin in an ELISA. A reduction of the complex formation to 50% is measured in the event of the peptide concentration being 4 μM whereas a peptide of LEF-1 with the amino acids Ile35–Val56 does not inhibit complex formation.

FIG. 4:

A substitution of acid amino acid residues and of phenylalanine in the minimum binding domain of LEF-1 blocks the translocation of β-catenin into the cell nucleus.

A. MDCK cells were transfected with wild type and mutants of LEF-1 and the translocation of endogenous β-catenin into the cell nucleus was checked by an immunofluorescence detection. The substitution of the acid amino acid residues of Asp19, Glu20, Asp26 and Glu27 by alanine blocks the translocation of β-catenin into the cell nucleus; the substitution of the aromatic amino acid Phe24 has the same effect. The substitution of Glu 14 and Lys25 does not prevent a translocation. Arrows mark the cells transfected by LEF-1 in the immunodetection for endogenic β-catenin.

"Comparison of the minimum binding domains of LEF-1 (SEQ ID NO:2) and TCF-4 (SEQ ID NO:4) with the respective positions of the amino acids."

FIGS. 5a–5e:

Mutations of alanine in the armadillo domain of β-catenin resulting in a reduction of more than 70% of the interaction with LEF-1, APC, conductin and E-cadherin.

The localization of the mutations related to the structural context (Helix 1–3, in frames) is represented. The figures above the amino acids in the sequence mark the analyzed mutants. The mutants with a reduction of the interaction with LEF-1 (red), APC (blue), conductin (green) and E-cadherin (yellow) of more than 70% are marked by various colours. Amino acids marked grey represent in all repeals preserved identical or chemically similar amino acids.

FIG. 6:

Mutations in the armadillo domain of β-catenin preventing specifically only binding of LEF-1, APC, conductin and e-cadherin.

Representation of the armadillo domain repeats 3–8 with mutations showing a reduction of the respective interaction to less than 30% (red) or to 30–60% (yellow). Mutants which are specific for the respective interaction: Arg469 and His470 for binding LEF-1, Trp383 for APC (20 amino acid repeats). Arg386 for APC (15 amino acid repeals), Phe253, Arg274 and Trp338 for conduct in are marked by arrows. The interactions were determined in a yeast 2-hybrid system by means of the β-galactosidase reporter activity.

FIG. 7:

Characterization of a hydrophobic pocket adjacent to the essential binding sites of β-catenin for LEF-1/TCF A. View of the hydrophobic pocket at the molecule surface of β-catenin (RasMol). The pocket is flanked by amino acids marked in orange or yellow colours. The amino acid residues of the essential binding site for LEF/TCF are marked in blue colour. The respective amino acids have been marked.

B. Side view of hydrophobic pocket.

Figure 8:
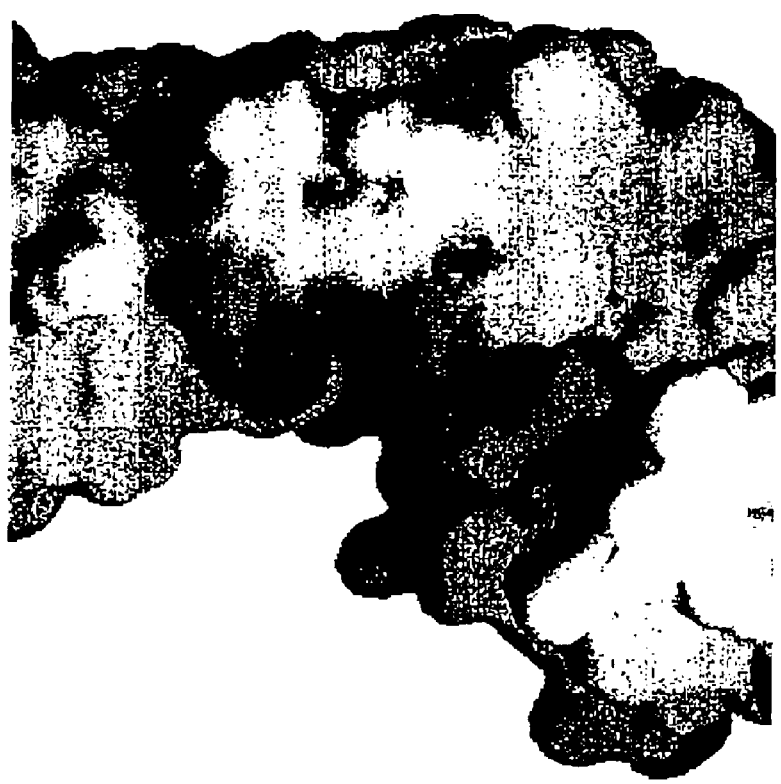
Figure 8:
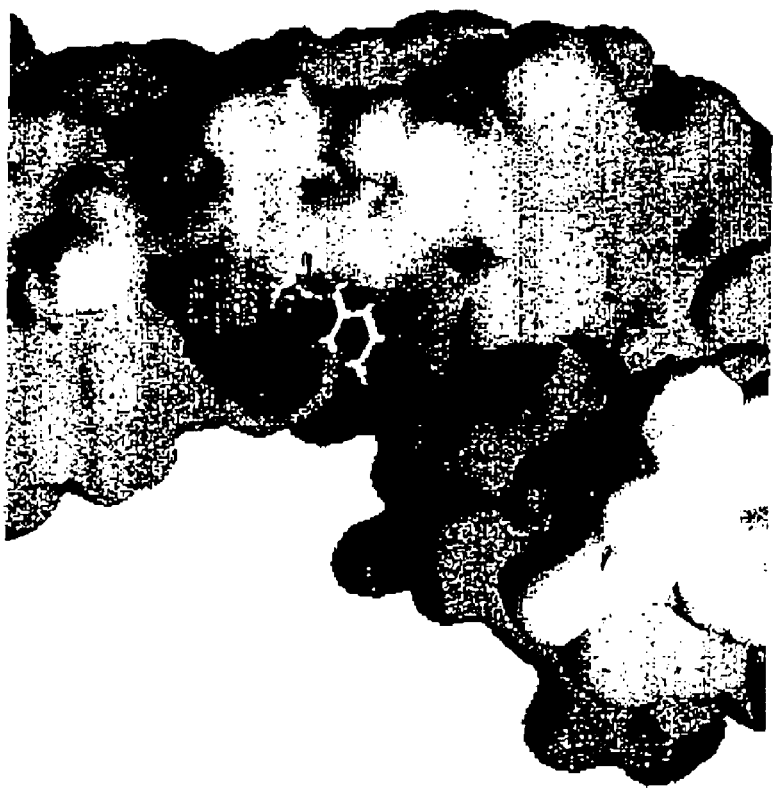
Figure 9:
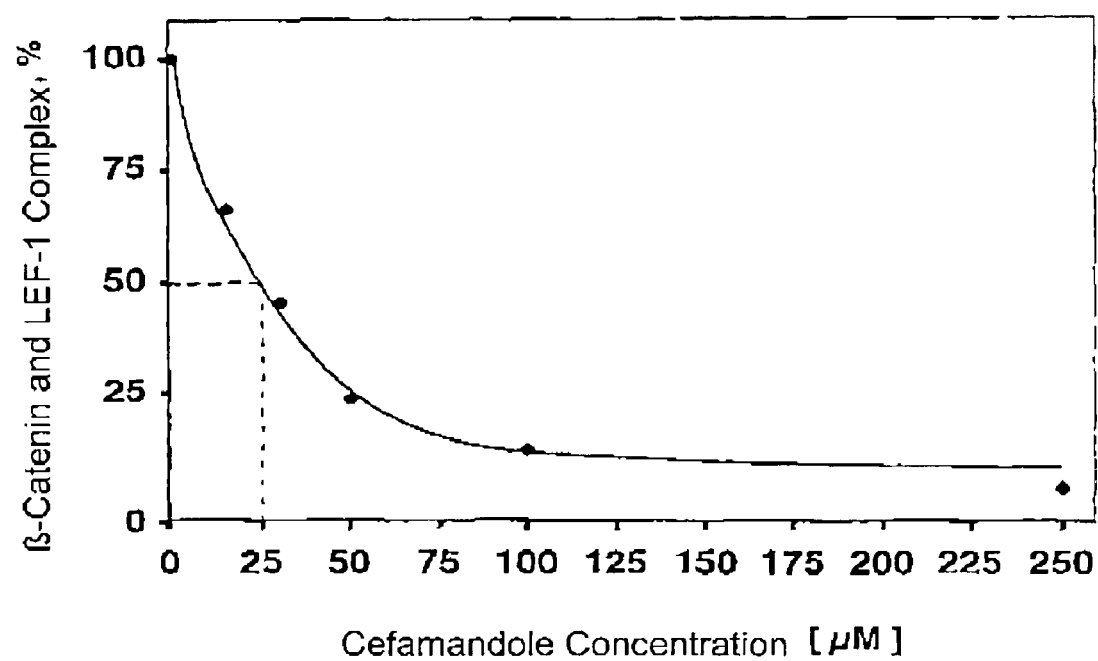

FIGS. 8A and 8B:

Substances binding in the hydrophobic pocket of β-catenin. Representation of the surface of the hydrophobic pocket region (Grasp). The amino acid residues of the essential binding site for LEF/TCF are marked in blue color (for mutations blocking the interaction between β-catenin and LEF/TCF: Lys 435, Arg 469 and His 470). In the β-catenin molecule one of the low-molecular substances binding in the pocket is represented.

FIG. 9:

Cefamandole as a representative of molecule class I inhibits the complex formation of LEF-1 and β-catenin in an ELISA.

Rising concentrations of cefamandole (15–250μM) result in a reduction of the complex formation of LEF-1 and β-catenin protein prepared recombinantly and purified in an ELISA (IC50=25 μM).

Tab. 1:

Amino acid sequence of the armadillo repeats 3–8 of human β-catenin: arm 3 (SEQ ID NO:6), arm 4 (SEQ ID NO:7), arm 5 (SEQ ID NO:8), arm 6 (SEQ ID NO:9), arm 7 (SEQ ID NO: 10), arm 8 (SEQ ID NO: 11) and arm 9 (SEQ ID NO: 12).

Tab. 2:

Compilation of all 1-catenin mutants with a binding activity of less than 60% towards the binding domains of LEF-1, APC, conductin and E-cadherin indicated.

Tab. 3:

Substances potentially binding in the hydrophobic pocket ("drug, list").

Tab. 4:

"Positive list" of substances inhibiting the complex formation or stopping the inhibition by competition around the binding site in the pocket.

Tab. 1

Amino acid sequence of the human β-catenin (armadillo repeats 3–8).

TABLE 2

Interaction between β-catenin mutants and LEF-1, APC(20 and 15 amino acid repeats). conductin and E-cadherin

| β-catenin mutants | arm, units | LEF-1 | APC-20 | interaction with APC-15 | conductin | E-cadherin |
| --- | --- | --- | --- | --- | --- | --- |

The values give the share of the respective interaction with the wild type β-catenin in percent. Interactions marked by - correspond to 60–100% of the wild type interaction. The values were determined in yeast 2-hybrid assays.

FIG. 1
Binding to β-catenin
(β-galactosidase units)

FIG. 2
Inhibition of binding of β-catenin

FIG. 3
Inhibition of the interaction between LEF-1 and β-catenin by synthetic peptides from the minimum binding area FIG. 5
β-catenin mutations with <30% of transactivation FIG. 6
Interaction between β-catenin mutants with:
Interaction reporter activity
Mutation for interaction partners specific

TABLE 1

Amino Acid Sequence of the Human β-catenin (Armidillo Repeats 3–8)

```
arm 3 (224–264)
His Arg Glu Gly Leu Leu Ala Ile Phe Lys Ser Gly Gly Ile Pro Ala Leu Val Lys Met Leu
Gly Ser Pro Val Asp Ser Val Leu Phe Tyr Ala Ile Thr Thr Leu His Asn Leu Leu Leu
(SEQ ID NO.: 6)

arm 4 (265–306)
His Gln Glu Gly Ala Met Ala Val Arg Leu Ala Gly Gly Leu Gln Lys Met Val Ala Leu
Leu Asn Lys Thr Asn Val Lys Phe Leu Ala Ile Thr Thr Asp Cys Leu Gln Ile Leu Ala Tyr
(SEQ ID NO.: 7)

arm 5 (307–349)
Gly Asn Gln Glu Ser Lys Leu Ile Ile Leu Ala Ser Gly Gly Pro Gln Ala Leu Val Asn Ile
Met Arg Thr Tyr Thr Tyr Glu Lys Leu Leu Try Thr Thr Ser Arg Val Leu Lys Val Leu
Ser Val (SEQ ID NO.: 8)

arm 6 (350–390)
Cys Ser Ser Asn Lys Pro Ala Ile Val Glu Ala Gly Gly Met Gln Ala Leu Gly Leu His Leu
Thr Asp Pro Ser Gln Arg Leu Val Gln Asn Cys Leu Trp Thr Leu Arg Asn Leu Ser Asp
(SEQ ID NO.: 9)

arm 7 (391–429)
Ala Ala Thr Lys Gln Glu Gly Met Glu Gly Leu Leu Gly Thr Leu Val Gln Leu Leu Gly
Ser Asp Asp Ile Asn Val Val Thr Cys Ala Ala Gly Ile Leu Ser Asn Leu Thr Cys
(SEQ ID NO.: 10)

arm 8 (430–473)
Asn Asn Tyr Lys Asn Lys Met Met Val Cys Gln Val Gly Gly Ile Glu Ala Leu Val Arg
Thr Val Leu Arg Ala Gly Asp Arg Glu Asp Ile Thr Glu Pro Ala Ile Cys Ala Leu Arg His
Leu Thr Ser (SEQ ID NO.: 11)
```

TABLE 1-continued

Amino Acid Sequence of the Human β-catenin (Armidillo Repeats 3-8)

```
arm 9 (474-519)
Arg His Gln Glu Ala Glu Met Ala Gln Asn Ala Val Arg Leu His Tyr Gly Leu Pro Val
Val Val Lys Leu Leu His Pro Pro Ser His Trp Pro Leu Ile Lys Ala Thr Val Gly Leu Ile
Arg Asn Leu Ala Leu (SEQ ID NO.: 12)
```

TABLE 2

Interaction between β-Catenin Mutants and LEF-1, APC (20 and 15 Amino Acid Repeats), Conductin and E-Cadherin

| β-Catenin Mutants | arm. units | Interaction With | | | | |
|---|---|---|---|---|---|---|
| | | LEF-1 | APC-20 | APC-15 | Conductin | E-Cadherin |
| Phe 253 | 3 | — | 40 | — | 17 | — |
| His 260 | 3 | 50 | 40 | 100 | 10 | 100 |
| Arg 274 | 4 | — | 40 | — | 29 | 50 |
| Lys 292 | 4 | — | 28 | — | 5 | — |
| Trp 338 | 5 | — | 55 | — | 20 | — |
| Arg 342 | 5 | — | 29 | — | 20 | 41 |
| Lys 345 | 5 | 38 | 0 | — | 22 | 27 |
| Lys 354 | 6 | 38 | — | 54 | 43 | 40 |
| Trp 383 | 6 | — | 0 | 59 | — | — |
| Arg 386 | 6 | 35 | — | 12 | 45 | — |
| Lys 394 | 7 | — | — | — | 42 | — |
| Lys 435 | 8 | — | — | 30 | 42 | — |
| Arg 457 | 8 | — | — | — | 36 | — |
| Arg 469 | 8 | 17 | — | — | — | 50 |
| His 470 | 8 | 2 | 47 | 60 | — | — |

The values give the share of the respective interaction with the wild type β-catenin in percent. Interactions marked by — correspond to 60–100% of the wild type interaction. The values were determined in yeast 2-hybrid assays.

TABLE 3

Drugs List 2000

| Molecule structure | Substance name | MDL-No. |
|---|---|---|
| 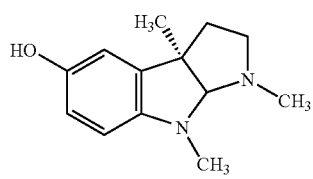 | (−)-ESEROLINE FUMARATE | MFCD00055202 |

TABLE 3-continued

Drugs List 2000

| Molecule structure | Substance name | MDL-No. |
| --- | --- | --- |
| | N-ACETYL-MURAMYL-ALA-ISOGLN-OH | MFCD00065478 |
| | 3,6-DIHYDROXY-BENZONORBORNANE | MFCD00077441 |
| | N-ACETYL-MURAMYL-ALA-D-ISOGLN-OH | MFCD00077638 |
| | (−)-COTININE | MFCD00077696 |
| | CEFAMANDOLE SODIUM SALT | MFCD00082385 |
| | (+/−)-NICOTINE-D3 SALICYLATE SALT | MFCD00083448 |

TABLE 3-continued

Drugs List 2000

| Molecule structure | Substance name | MDL-No. |
| --- | --- | --- |
| | BENZYL 1,2-DIPHENYL-4-HYDROXY-5-OXO-3-PYRROLINE-3-CARBOXYLATE | MFCD00088051 |
| | 1-(4-FLUOROPHENYL)-3-PHENYLPYRROLIDINE-2,5-DIONE | MFCD00097831 |
| | 3-PHENYL-1-(2-THIENYLMETHYL)PYRROLIDINE-2,5-DIONE | MFCD00097832 |
| | N1-(4-[2,5-DIOXO-1-[4-TRIFLUOROMETHOXY)PHENYL]TETRAHYDRO-1H-PYRROL-3-YL]PHENYL)-2,2,2-TRIFLUOROACETAMIDE | MFCD000100474 |
| | 1,3-DIPHENYLCYCLOPENTANE-2,4,5-TRIONE | MFCD000101320 |
| | ETHYL 2-OXO-2-[(2-OXOAZEPAN-3-YL)AMINO]ACETATE | MFCD000103142 |
| | 3-BENZOYL-1,2,3,10B-TETRAHYDRO-PYRROLO(2,1-A)ISOQUINOLINE-1-CARBONITRILE | MFCD000123443 |

TABLE 3-continued
Drugs List 2000
| Molecule structure | Substance name | MDL-No. |
|---|---|---|
| 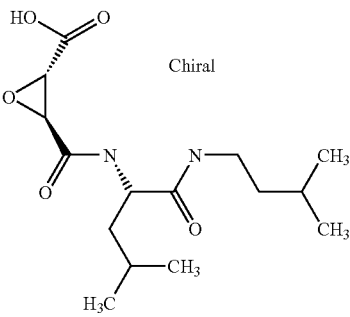 | L-TRANS-EPOXYSUCCINYL-LEU-3-METHYLBUTYLAMIDE | MFCD000132882 |
| 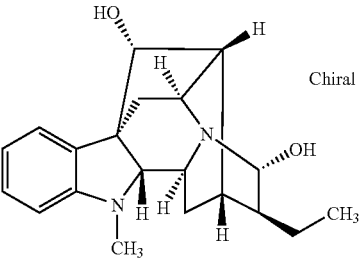 | AJMALINE | MFCD000135652 |
| 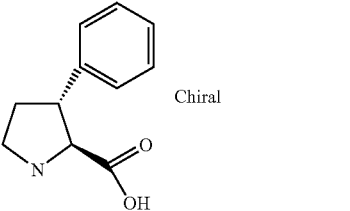 | (2S,3R)-3-PHENYLPYRROLIDINE-2-CARBOXYLIC ACID | MFCD000142984 |
| 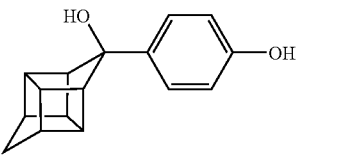 | 4-(2-HYDROXYOCTAHYDRO-1,3,4-METHENO-2H-CYCLOBUTA(CD)PENTALEN-2-YL)PHENOL | MFCD000155174 |
| 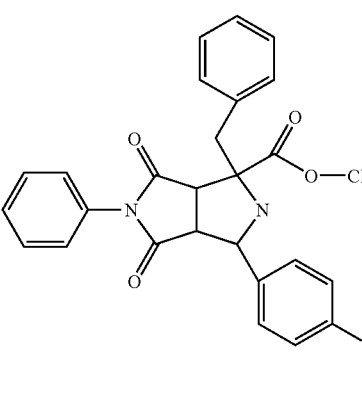 | METHYL C-4-(4-METHOXYPHENYL)-2-BENZYL-7-PHENYL-6,8-DIOXO-3,7-DIAZABICYCLO[3.3.0]-OCTANE-R-2-CARBOXYLATE | MFCD000202518 |

TABLE 3-continued

Drugs List 2000

| Molecule structure | Substance name | MDL-No. |
|---|---|---|
| 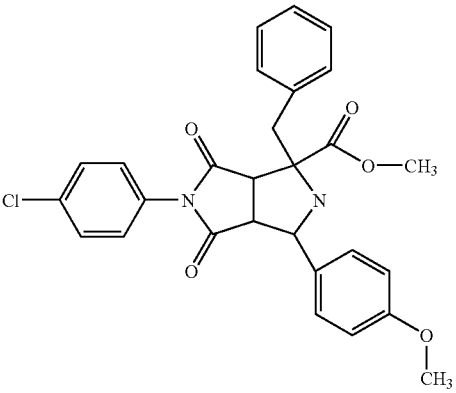 | METHYL C-4-(4-METHOXYPHENYL)-2-BENZYL-7-(4-CHLOROPHENYL)-6,8-DIOXO-3,7-DIAZABICYCLO[3.3.0]-OCTANE-R-2-CARBOXYLATE | MFCD000202519 |
| 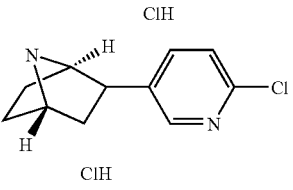 | (+/−)-EPIBATIDINE DIHYDROCHLORIDE | MFCD000210196 |
| 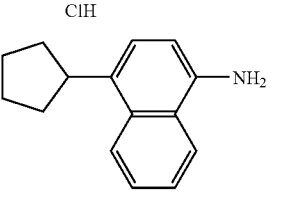 | 4-CYCLOPENTYL-NAPHTHALEN-1-YLAMINE, HYDROCHLORIDE | MFCD000227852 |
| 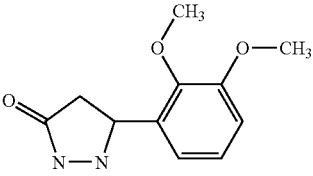 | 5-(2,3-DIMETHOXY-PHENYL)-PYRAZOLIDIN-3-ONE | MFCD000228403 |
| 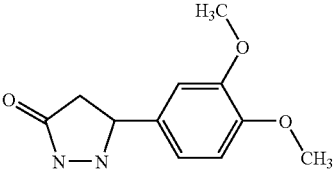 | 5-(3,4-DIMETHOXY-PHENYL)-PYRAZOLIDIN-3-ONE | MFCD000229211 |
| 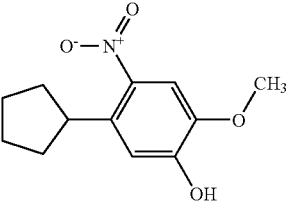 | 5-CYCLOPENTYL-2-METHOXY-4-NITRO-PHENOL | MFCD000230901 |

TABLE 3-continued

Drugs List 2000

| Molecule structure | Substance name | MDL-No. |
|---|---|---|
| | AC-(6-O-STEAROYL)-MURAMYL-ALA-D-ISOGLUTAMINE | MFCD000236777 |
| | ANTHO-RNAMIDE | MFCD000236789 |
| | 1,3,5(10),6,8(14BETA)-ESTRAPENTAEN-3-OL-17-ONE ACETATE | MFCD000271642 |
| | NORFLUOROCURARINE | MFCD000274483 |

TABLE 3-continued

Drugs List 2000

| Molecule structure | Substance name | MDL-No. |
|---|---|---|
| | 4,5-DIPHENYLPYRAZOLIDIN-3-ONE | MFCD000277796 |
| | 4-(4-METHOXY-PHENYL)-2-OXO-PYRROLIDINE-3-CARBOXYLIC ACID | MFCD000297824 |
| | (+)-EPIBATIDINE HYDROCHLORIDE | MFCD000467208 |
| | FLUOROCURARINE CHLORIDE | MFCD000467712 |
| | (1'S,2'S)-NICOTINE 1'-OXIDE | MFCD000869528 |

TABLE 3-continued
Drugs List 2000
| Molecule structure | Substance name | MDL-No. |
|---|---|---|
| | SPECS SPECS CIF 7952 | MFCD0001114864 |
| | 2-ETHYL-2-(3-METHOXYPHENYL)PYRROLIDINE | MFCD0001314146 |
| | N-(TERT-BUTYL)-2-(ISOXAZOL-5-YLCARBONYL)DECAHYDROISOQUINOLINE-3-CARBOXAMIDE | MFCD0001314517 |
TABLE 4
Positive List
Molecule Class IA (Inhibitors of the Cefamandole-type)
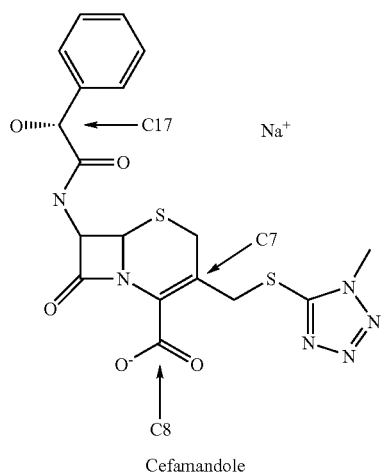
Cefamandole
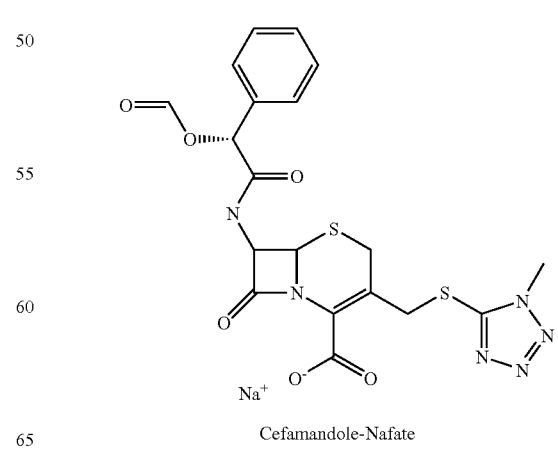
Cefamandole-Nafate TABLE 4-continued Positive List

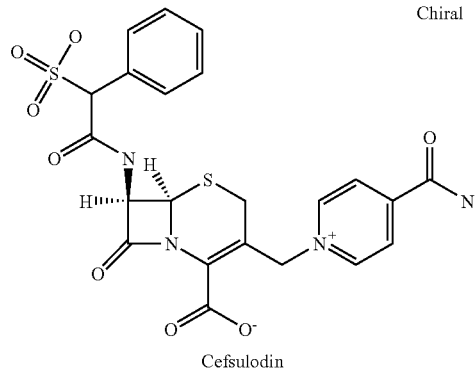

Cefsulodin

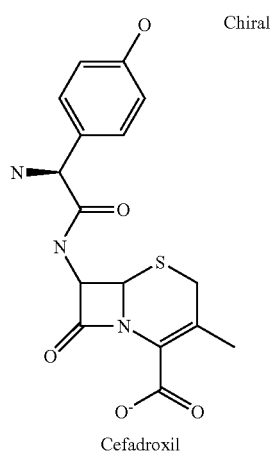

Cefadroxil

Molecule Class IB

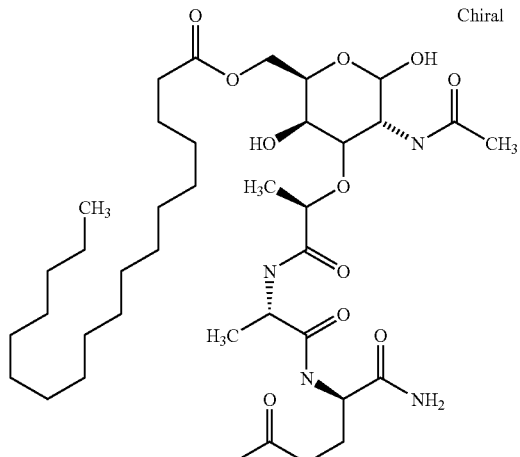

AC-(6-O-STEAROYL)-MURAMYL-ALA-D-ISOGLUTAMINE

TABLE 4-continued

Positive List

Molecule Class IC

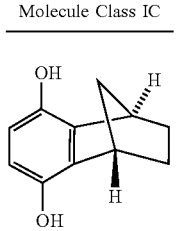

3,6-DIHYDROXYBENZONORBORNANE

Molecule with Modulating Activity for Molecule Class 1

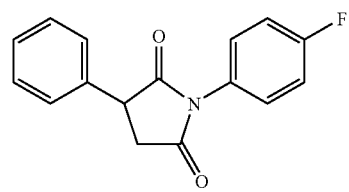

1-(4-FLUOROPHENYL)-3-PHENYLPYRROLIDINE-2,5-DIONE

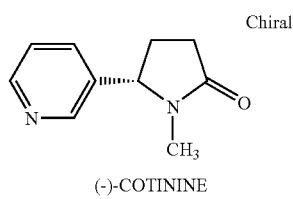

(-)-COTININE

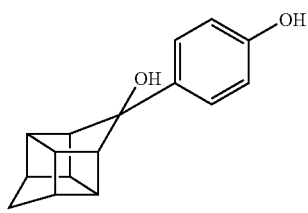

4-(2-HYDROXYOCTAHYDRO-1,3,4-METHENO-
2H-CYCLOBUTA(CD)PENTALEN-2-YL)PHENOL

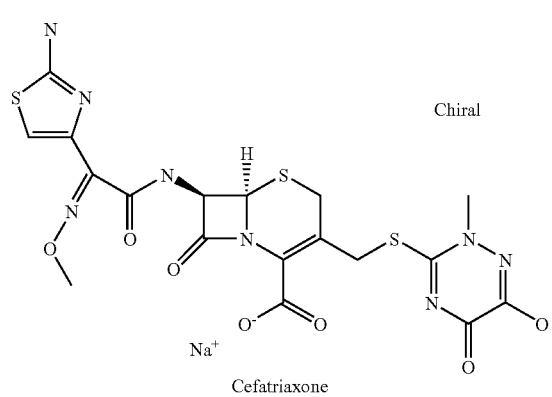

Cefatriaxone

TABLE 4-continued

Positive List

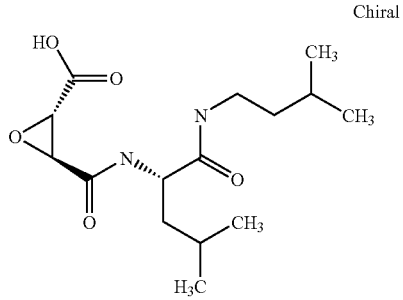

L-TRANS-EPOXYSUCCINYL-LEU-3-METHYLBUTYLAMIDE

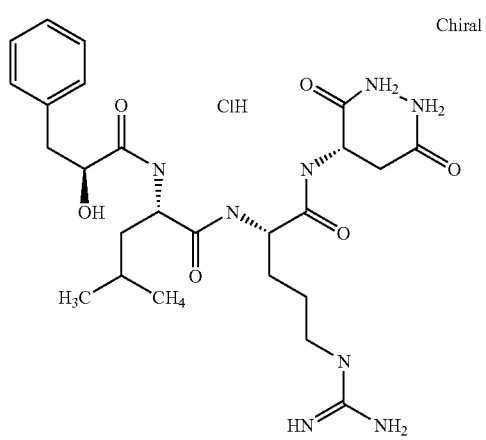

ANTHO-RNAMIDE

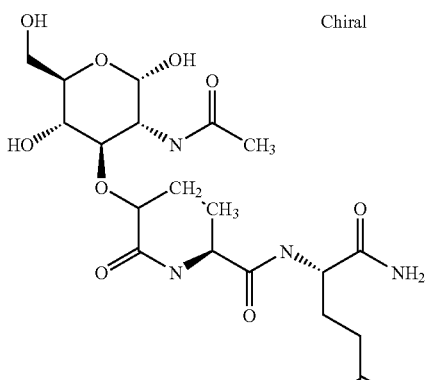

N-ACETYL-MURAMYL-ALA-ISOGLN-OH

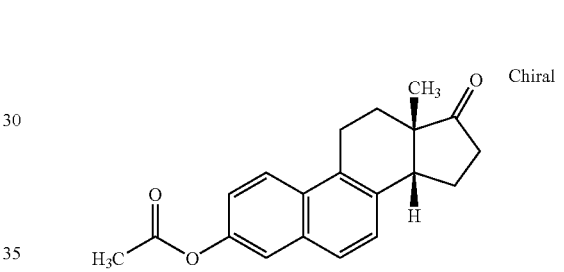

1,3,5,(10),6,8(14BETA)-ESTRAPENTAEN-3-OL-17-ONE ACETATE

---

The invention claimed is:

1. A peptide or polypeptide obtained from the armadillo domain of human β-catenin polypeptide which inhibits the interaction of human β-catenin polypeptide and a transcription factor or tumor suppressor protein, wherein said peptide or polypeptide is selected from the group consisting of peptides or polypeptides consisting of the sequences shown in SEQ ID NO: 6, SEQ ID NO: 7, SEQ ID NO: 8, SEQ ID NO: 9, SEQ ID NO: 10, SEQ ID NO: 11, and SEQ ID NO: 12.

2. A peptide or polypeptide obtained from the armadillo domain of human β-catenin polypeptide which inhibits the interaction of human β-catenin polypeptide and a transcription factor or tumor suppressor protein, wherein said peptide or polypeptide is selected from the group consisting of peptides or polypeptides consisting of the sequences shown in SEQ ID NO: 6 having a mutation in Phe in position 30, a mutation in His in position 37 or both; SEQ ID NO: 7 having a mutation in Arg in position 9, a mutation in Lys in position 27 or both; SEQ ID NO: 8 having a mutation in Trp in position 32, a mutation in Arg in position 36, a mutation in Lys in position 39 or any combination of mutations thereof; SEQ ID NO: 9 having a mutation in Lys in position 5, a mutation in Trp in position 34, a mutation in Arg in position 37 or any combination of mutations thereof; SEQ ID NO: 10 having a mutation in Lys in position 4; and SEQ ID NO: 11 having a mutation in Lys in position 6, a mutation in Arg in position 28, a mutation in Arg in position 40, a mutation in His in position 41 or any combination of mutations thereof, wherein said mutation replaces the indicated amino acid with an aliphatic amino acid.

3. The peptide or polypeptide according to claim 2, wherein said mutation replaces the indicated amino acid with alanine, valine, leucine or isoleucine.

4. The mutant according to claim 2, wherein said mutation replaces the indicated amino acid with alanine.

5. The peptide of claim 3, wherein said transcription factor or tumor suppressor protein is selected from the group consisting of lymphoid enhancer-binding factor-1 (LEF-1), T cell transcription factor-1 (TCF-1), 15 amino acid repeats of adenomatous polyposis coli (APC-15), conductin, E-cadherin and 20 amino acid repeats of APC (APC-20).

* * * * *

UNITED STATES PATENT AND TRADEMARK OFFICE
CERTIFICATE OF CORRECTION

PATENT NO. : 7,067,474 B1
APPLICATION NO. : 09/641104
DATED : June 27, 2006
INVENTOR(S) : Walter Birchmeier and Jens-Peter Von Kries It is certified that error appears in the above-identified patent and that said Letters Patent is hereby corrected as shown below:

Column 1,
Line 16, "LEF-1-TCF-4" should read --LEF-1-/TCF-4--.
Line 30, "α-catenin" should read --β-catenin--.
Line 33, "α-catenin" should read --β-catenin--.
Line 36, "α-catenin" should read --β-catenin--.
Line 37, "α-catenin" should read --β-catenin--.
Line 41, "α-catenin" should read --β-catenin--.
Line 45, "beta-cantenin-Tef" should read --beta-catenin-Tcf--.
Line 54-55, "mutation. % in" should read --mutations in--.
Line 55, "α-catenin" should read --β-catenin--.
Line 56, "α-catenin" should read --β-catenin--.
Line 57, "beta-catenin-Tef" should read --beta-catenin-Tcf--.

Column 3,
Line 51, "β-catenin produced" should read --β-catenin were produced--.

Column 4,
Line 32, "corresponds t)" should read --corresponds to--.

Column 5,
Line 14, "LEF-TCF" should read --LEF-1/TCF--.
Line 52, "averaged (or" should read --averaged for--.

Column 6,
Line 7, "endogenic & catenin" should read --endogenic β-catenin--.
Line 42, "405 mm" should read --405 nm--.
Line 63, "Leu218-Leu71 µl or" should read --Leu218-Leu781 or--.

Column 7,
Line 4, "Ser1259Asp 1400" should read --Ser1259-Asp 1400--.

Column 8,
Line 1, ""Comparison of the" should read --B. Comparison of the--.
Line 3, "amino acids."" should read --amino acids.--
Line 15, "in all repeals" should read --in all repeats--.
Lines 44-45, "Substances binding in the hydrophobic pocket of β-catenin. Representation of the" should read --Substances binding in the hydrophobic pocket of β-catenin.
A. Representation of the--.

UNITED STATES PATENT AND TRADEMARK OFFICE
CERTIFICATE OF CORRECTION

| | |
|---|---|
| PATENT NO. | : 7,067,474 B1 |
| APPLICATION NO. | : 09/641104 |
| DATED | : June 27, 2006 |
| INVENTOR(S) | : Walter Birchmeier and Jens-Peter Von Kries |

It is certified that error appears in the above-identified patent and that said Letters Patent is hereby corrected as shown below:

Column 9,
Line 2, "1-catenin" should read --β-catenin--.
Line 7, ""("drug, list")" should read --("drug list")--.

Signed and Sealed this

Thirtieth Day of January, 2007

JON W. DUDAS
*Director of the United States Patent and Trademark Office*

```
                        SEQUENCE LISTING

<160> NUMBER OF SEQ ID NOS: 12

<210> SEQ ID NO 1
<211> LENGTH: 24
<212> TYPE: PRT
<213> ORGANISM: Artificial Sequence
<220> FEATURE:
<223> OTHER INFORMATION: Description of Artificial Sequence: Peptide
      from LEF-1

<400> SEQUENCE: 1

Gly Asp Pro Glu Leu Cys Ala Thr Asp Glu Met Ile Pro Phe Lys Asp
 1               5                  10                  15

Glu Gly Asp Pro Gln Lys Glu Lys
            20

<210> SEQ ID NO 2
<211> LENGTH: 14
<212> TYPE: PRT
<213> ORGANISM: Artificial Sequence
<220> FEATURE:
<223> OTHER INFORMATION: Description of Artificial Sequence: Peptide
```

-continued

```
      from LEF-1

<400> SEQUENCE: 2

Glu Leu Cys Ala Thr Asp Glu Met Ile Pro Phe Lys Asp Glu
 1               5                  10

<210> SEQ ID NO 3
<211> LENGTH: 23
<212> TYPE: PRT
<213> ORGANISM: Artificial Sequence
<220> FEATURE:
<223> OTHER INFORMATION: Description of Artificial Sequence: Peptide
      from TCF-4

<400> SEQUENCE: 3

Gly Gly Asp Asp Leu Gly Ala Asn Asp Glu Leu Ile Ser Phe Lys Asp
 1               5                  10                  15

Glu Gly Glu Gln Glu Glu Lys
            20

<210> SEQ ID NO 4
<211> LENGTH: 14
<212> TYPE: PRT
<213> ORGANISM: Artificial Sequence
<220> FEATURE:
<223> OTHER INFORMATION: Description of Artificial Sequence: Peptide
      from TCF-4

<400> SEQUENCE: 4

Asp Leu Gly Ala Asn Asp Glu Leu Ile Ser Phe Lys Asp Glu
 1               5                  10

<210> SEQ ID NO 5
<211> LENGTH: 16
<212> TYPE: PRT
<213> ORGANISM: Artificial Sequence
<220> FEATURE:
<223> OTHER INFORMATION: Description of Artificial Sequence:
      Antennapediapeptide

<400> SEQUENCE: 5

Arg Gln Ile Glu Ile Trp Phe Gln Asn Arg Arg Met Lys Trp Lys Glu
 1               5                  10                  15

<210> SEQ ID NO 6
<211> LENGTH: 41
<212> TYPE: PRT
<213> ORGANISM: Artificial Sequence
<220> FEATURE:
<223> OTHER INFORMATION: Description of Artificial Sequence: Armadillo
      repeat 3 of human β-catenin

<400> SEQUENCE: 6

His Arg Glu Gly Leu Leu Ala Ile Phe Lys Ser Gly Gly Ile Pro Ala
 1               5                  10                  15

Leu Val Lys Met Leu Gly Ser Pro Val Asp Ser Val Leu Phe Tyr Ala
            20                  25                  30

Ile Thr Thr Leu His Asn Leu Leu Leu
            35                  40

<210> SEQ ID NO 7
<211> LENGTH: 41
<212> TYPE: PRT
<213> ORGANISM: Artificial Sequence
<220> FEATURE:
<223> OTHER INFORMATION: Description of Artificial Sequence: Armadillo
``` repeat 4 of human β-catenin

<400> SEQUENCE: 7

His Gln Glu Gly Ala Met Ala Val Arg Leu Ala Gly Gly Leu Gln Lys
1               5                   10                  15

Met Val Ala Leu Leu Asn Lys Thr Asn Val Lys Phe Leu Ala Ile Thr
            20                  25                  30

Thr Asp Cys Leu Gln Ile Leu Ala Tyr
        35                  40

<210> SEQ ID NO 8
<211> LENGTH: 43
<212> TYPE: PRT
<213> ORGANISM: Artificial Sequence
<220> FEATURE:
<223> OTHER INFORMATION: Description of Artificial Sequence: Armadillo
      repeat 5 of human β-catenin

<400> SEQUENCE: 8

Gly Asn Gln Glu Ser Lys Leu Ile Ile Leu Ala Ser Gly Gly Pro Gln
1               5                   10                  15

Ala Leu Val Asn Ile Met Arg Thr Tyr Thr Tyr Glu Lys Leu Leu Trp
            20                  25                  30

Thr Thr Ser Arg Val Leu Lys Val Leu Ser Val
        35                  40

<210> SEQ ID NO 9
<211> LENGTH: 41
<212> TYPE: PRT
<213> ORGANISM: Artificial Sequence
<220> FEATURE:
<223> OTHER INFORMATION: Description of Artificial Sequence: Armadillo
      repeat 6 of human β-catenin

<400> SEQUENCE: 9

Cys Ser Ser Asn Lys Pro Ala Ile Val Glu Ala Gly Gly Met Gln Ala
1               5                   10                  15

Leu Gly Leu His Leu Thr Asp Pro Ser Gln Arg Leu Val Gln Asn Cys
            20                  25                  30

Leu Trp Thr Leu Arg Asn Leu Ser Asp
        35                  40

<210> SEQ ID NO 10
<211> LENGTH: 39
<212> TYPE: PRT
<213> ORGANISM: Artificial Sequence
<220> FEATURE:
<223> OTHER INFORMATION: Description of Artificial Sequence: Armadillo
      repeat 7 of human β-catenin

<400> SEQUENCE: 10

Ala Ala Thr Lys Gln Glu Gly Met Glu Gly Leu Leu Gly Thr Leu Val
1               5                   10                  15

Gln Leu Leu Gly Ser Asp Asp Ile Asn Val Val Thr Cys Ala Ala Gly
            20                  25                  30

Ile Leu Ser Asn Leu Thr Cys
        35

<210> SEQ ID NO 11
<211> LENGTH: 44
<212> TYPE: PRT
<213> ORGANISM: Artificial Sequence
<220> FEATURE:

-continued

```
<223> OTHER INFORMATION: Description of Artificial Sequence: Armadillo
      repeat 8 of human β-catenin

<400> SEQUENCE: 11

Asn Asn Tyr Lys Asn Lys Met Met Val Cys Gln Val Gly Gly Ile Glu
 1               5                  10                  15

Ala Leu Val Arg Thr Val Leu Arg Ala Gly Asp Arg Glu Asp Ile Thr
            20                  25                  30

Glu Pro Ala Ile Cys Ala Leu Arg His Leu Thr Ser
        35                  40

<210> SEQ ID NO 12
<211> LENGTH: 46
<212> TYPE: PRT
<213> ORGANISM: Artificial Sequence
<220> FEATURE:
<223> OTHER INFORMATION: Description of Artificial Sequence: Armadillo
      repeat 9 of human β-catenin

<400> SEQUENCE: 12

Arg His Gln Glu Ala Glu Met Ala Gln Asn Ala Val Arg Leu His Tyr
 1               5                  10                  15

Gly Leu Pro Val Val Lys Leu Leu His Pro Pro Ser His Trp Pro
            20                  25                  30

Leu Ile Lys Ala Thr Val Gly Leu Ile Arg Asn Leu Ala Leu
        35                  40                  45
```